United States Patent
Cid Vivanco et al.

(10) Patent No.: US 9,770,477 B2
(45) Date of Patent: Sep. 26, 2017

(54) NATURAL ANTIOXIDANT ANTI-INFLUENZA COMPOSITION

(75) Inventors: Roberto Francisco Cid Vivanco, Quito (EC); Edwin Renato Andrade Bejarano, Quito (EC)

(73) Assignee: PHARMABRAND S.A., Quito (EC)

( * ) Notice: Subject to any disclaimer, the term of this patent is extended or adjusted under 35 U.S.C. 154(b) by 758 days.

(21) Appl. No.: 14/342,600

(22) PCT Filed: Aug. 31, 2012

(86) PCT No.: PCT/EC2012/000027
§ 371 (c)(1),
(2), (4) Date: May 20, 2014

(87) PCT Pub. No.: WO2013/029634
PCT Pub. Date: Mar. 7, 2013

(65) Prior Publication Data
US 2014/0248318 A1    Sep. 4, 2014

(30) Foreign Application Priority Data
Sep. 3, 2011 (EC) .................................. 11-11303

(51) Int. Cl.
*A61K 36/28* (2006.01)
*A61K 36/61* (2006.01)
*A61K 9/20* (2006.01)

(52) U.S. Cl.
CPC ............ *A61K 36/28* (2013.01); *A61K 9/2018* (2013.01); *A61K 36/61* (2013.01)

(58) Field of Classification Search
USPC ......................................................... 424/737
IPC .............................................. A61K 36/28,36/61
See application file for complete search history.

(56) References Cited

U.S. PATENT DOCUMENTS

| 2006/0104926 A1 | 5/2006 | Nagamine et al. |
| 2006/0104927 A1 | 5/2006 | Nagamine et al. |
| 2006/0112584 A1* | 6/2006 | Jones ....................... A23B 7/02 34/60 |
| 2012/0027838 A1* | 2/2012 | Gordon ................ A61K 9/0056 424/443 |

FOREIGN PATENT DOCUMENTS

DE    20 2007 008 818 U1 *  8/2008
WO    02/47703 A2     6/2002

OTHER PUBLICATIONS

Bauer, R. et al. "Echinacea purpurea" Echinaces Handbuch for Aerzte, Apotheker and andere Naturwissenschaftler, 1990.
Mistrikova, I. et al. "Echinacea—chemical composition, immunostimulatory activities and uses", Thaiszia—Journal of Botany, vol. 16, pp. 11-26, 2006.

\* cited by examiner

*Primary Examiner* — Chris R Tate
(74) *Attorney, Agent, or Firm* — Nath, Goldberg & Meyer; Joshua B. Goldberg; Tanya E. Harkins

(57) ABSTRACT

The invention relates to a composition from the extract of *Myrciaria dubia* and *Echinacea purpurea*, which has a synergistic effect. The composition of the invention has potentiated antioxidant and anti-flu properties, as well as a high immuno-stimulating capacity.

12 Claims, 2 Drawing Sheets

NATURAL ANTIOXIDANT ANTI-INFLUENZA COMPOSITION

This is a National Phase Application filed under 35 U.S.C. §371 as a national stage of International Application No. PCT/EC2012/000027, filed Aug. 31, 2012, claiming the benefit from Ecuador Patent Application No. SP-11-11303, filed Sep. 3, 2011, the entire content of each of which is hereby incorporated by reference in its entirety.

TECHNICAL FIELD

The invention relates to a composition from an extract of *Echinacea purpurea*, in which the composition has a high immune-stimulating and anti-inflammatory capacity, in synergism with an extract of *Myrciaria dubia*, which is the richest source of vitamin C in nature, further correlated with the appropriate concentration of cichoric acid and ellagic acid by which a potentiated antioxidant and immunostimulant effect is achieved.

BACKGROUND OF THE INVENTION

*Echinacea purpurea*

*Echinacea* sp. plant has been used as a natural medicine for many years up to the present. This genus corresponds to native North American plants which characterized by its red or purple flowers, however only three of them such as *Echinacea angustifolia, Echinacea pallida* and *Echinacea purpurea* are used for medical purposes.

In the field of medicinal plants, *Echinacea purpurea* is one of the most investigated plants, due to its properties as stimulant of immune system (Bauer and Wagner 1991). The therapeutic activity of the *E. purpurea* has been attributed to its content of caffeic acid, chlorogenic acid, echinacoside and lipophilic derivative compounds alkylamides.

Most of alkylamides are reported to act as potent inhibitors of cycloxygenase. Inhibitory properties of arachidonic acid on the metabolism are in accordance with the traditional use of the plant in the therapy of inflammatory diseases.

Among constituents of *Echinacea purpurea* has been described phenylpropanoids such as caffeic acid, derivatives as echinacoside, caftaric acid, chlorogenic acid (Bauer 1991). Additionally there are other constituents as flavonoids, including rutin whose highest concentration in leaves is in *E. purpurea*; the quercetin at 0.48% and with a minimum amount in *E. angustifolia*.

Further components are terpenoid compounds including borneol and some others which are unique to each species. Lipidic compounds, polyacetylenes have been partially elucidated and reported with a content of 2% in the roots and alkylamides which are mostly occurring in *E. purpurea* which is one of the differences with respect to other two *Echinaceas* sp species. There is a multitude of *Echinaceas* sp. developed for decorative purposes.

Other constituents found in *Echinaceas* sp. are reduced sugars, phytosterols and ascorbic acid in a concentration of 0.214%.

*Echinacea purpurea* is generally used to reduce inflammatory processes for example in arthritis and promotes the T-cells formation in inflammatory conditions of the skin in external use. In Germany, where the use of this plant was generalized, the plant was used for helping the organisms to resist flu infections and throat conditions in concomitance to the flu (Bradley 1992).

*Myrciaria dubia*

Some research evidences report that alkylamides have an immuno-stimulatory effect (Goel Y et. al. *Alkylamides of Echinacea purpurea Stimulate alveolar macrophage function in normal rats. International Inmunopharmacology* 2:381-387-2002). *Myrciaria dubia*, also known as Araza of water and camu camu is a fruit plant of bushy type native of the Amazon rainforest, existing in some Peruvian affluents of Amazon River and some affluent of provinces of Napo and Sucumbios in Ecuador. This plant grows wild along river banks of Ucayali, Pacaya and Napo rivers, and it is a much ramified shrub, under 3 m of height in size generally, with globose fruits with colouring varying from pink to dark red violet, containing 1 to 4 seeds covered by a mesh of white fibers, its fruits are characterized by their high vitamin C content, containing 2800 mg per 100 g of pulp (the orange contains an average of 60 mg per 100 g, depending of the variety) (Collazos C. White H. Composition of Peruvian foods).

This plant is considered the greatest Vitamin C natural source overcoming the Acerola, and its extract has applications as an antioxidant and recently in cosmetics as a whitening agent for spotted skins (Japanese Patent JP-A 9-221429).

Among the metabolites found in this Amazonian plant was found ellagic acid which is employed in the treatment of tumoral pathologies, due to its properties of generating apoptosis. Also are alpha pinene and d-limonene. This plant also has iron, niacin, riboflavin, calcium, and amino acids such as leucine, proline and serine.

The invention describes a composition comprising dry extracts of *Echinacea purpurea* and *Myrciaria dubia* having a synergistic effect for improving the immune response to infectious diseases including flu infections.

*Echinacea purpurea* has been used for years as a drug up to the present. As a medicine, have been used several extraction methods, including organic solvents and isolation by column chromatography. Some of its components such as isobutylamides have shown immuno-stimulatory activity, but when it is combined with metabolites of *Myrciaria dubia* including ellagic acid, the antioxidant activity is potentiated, i.e. unstable molecules of free radicals lose their destabilizing action and contribute to improve the pathologic process, especially when the human is under the action of virus and hostile pathogenic bacteria.

The flu, influenza or common cold caused by virus causes a loss of 10 billion dollar per year in the U.S.A despite all the support to the patient, such as analgesics, vaccines and drugs suggested for these cases.

The working time lost by this disease is an average of 3 days (Keech et. al The impact of influenza and influenza like illness on productivity and healthcare resources utilization on a working population. Occup Med (London) 1998, 48 85-90).

Influenza, flu, or common cold is a viral process potentially dangerous in children and elderlies, and to whom with pre-existing health problem. Every year, 500 million people are infected and about 5 million of these in a severe form, and reported 500 thousand of deaths (World Health Organization fact sheet-211, March 2003).

Usually, influenza has been treated with OTC products including analgesics, antihistamines, expectorants, decongestants, vaccines, which involve egg proteins and in some cases produce episodes of allergies; old generation antiviral as M2 channel blockers and subsequently with neuraminidase inhibitors. This whole arsenal seeks to reduce the severity of symptoms and shorten the period of illness. Side effects are known for everybody.

Flu complications lead to the patient being affected by pneumonia or bronchitis, so the recovery time can be extended to two months. Flu is an acute respiratory disease caused by flu virus, mainly affecting the respiratory tract (nose, throat and bronchi), the infection usually lasts a week and is mainly characterized by sudden appearance of high fever, myalgia, headache, weakness, cough, sore throat and rhinitis, most patients recover in 1 to 2 weeks without requiring medical treatment. The flu spreads rapidly around the world.

The influenza viruses are currently classified in two types A and B, and influenza virus A has shown an ability to cause pandemics. Pandemic viruses are caused by antigenic transfers, which are characterized by higher genetic changes in the hemagglutinin subtype, with or without change in neuraminidase.

In the XX century have been documented three major pandemics: Spanish flu 1918 by the influenza virus A (H1N1) with 20 million of dead, the Asian flu type A (H2N2), and the Hong Kong by the influenza type A (H3N2) in 1968. Currently these viruses are in circulation and it is expected to occur a new pandemic arising from the strain of virus that causes avian flu (H5N1).

Should a pandemic occur must meet the following conditions:
1. To occur the emergence of a flu strain for which a lot of people are not protected.
2. Transmission of the new virus from person to person quickly.
3. To cause disease in humans in massive scale.

Avian flu meets all these requirements. Flu with such characteristics can affect 20% of the world population. It has been reported cases of human infected in Asia.

In common flu, the incubation ranges from 1 to 4 days. The person who has flu is contagious from the day before the beginning of symptoms until seven days later, but in immunocompromised persons this period is greater.

The risk for a human to contracting the disease during the circulation of the virus depends of the following factors:
1. Virulence of the circulating strain.
2. Natural level of immunity, human general health and previous exposure to influenza virus or vaccination.
3. Basal or nutritional state.
4. Habitability; increased risk of transmission in closed spaces.
5. Age; common in people over 60 years and preschoolers.

The management of flu infection has as its object to help the immune system to eliminate the virus in a few days, usually bed rest and drink a lot of liquids are recommended. Vitamin C has been associated with improvement evolution of respiratory infections. The ethno-medicine uses garlic, lemon juice, thyme, eucalyptus or peppermint teas, which has antiviral action in vitro and the *Echinacea* sp for reducing the duration of flu. Further, homeopathy prescribes the *Oscillococcinum* which reduces the flu in a few days. General hygiene measures are indicated to avoid contagiousness.

Fever is an alarm mechanism that physiologically activates monocytes and various immune mediators but the use of antipyretics on flu in adults is controversial. As antivirals, amantadine and zanamivir are used for help to reduce the duration of flu symptoms in 1 or 2 days, their benefit is marginal. Zanamivir inhibits neuraminidase enzyme which blocks viral replication, another inhibitor used is oseltamivir.

Vaccination is a basic measure to prevent the flu and it is recommended for people over 60 years of age, or for whom which have high risk of complications as in the case of obstructive lung disease, chronic heart disease, chronic kidney disease or immunosuppression. In persons over 60 years of age non-hospitalized, vaccines reduce the morbidity in 60% and mortality in 70% mortality, and for hospitalized persons the effectiveness drops at 30-40%.

In patent literature of the previous art related to these plants individually, the *Echinacea purpurea* is mentioned in 152 patent documents.

*Myrciaria dubia* is mentioned in the following documents: US2006/0104927, JP 2005253307, JP 2004189698, JP 2001031558, JP 2000342162, JP 2000327525, JP 2000327553, JP 2000327552, JP 2000327550, JP 2000327549, JP 9215475, JP 11246336, JP 9221429, JP 9140341 and RU 2311190.

The state of the art is completely silent in relation to documents which include a combination of both extracts, namely, *Echinacea purpurea* and *Myrciaria dubia*.

In the prior art there are published dissimilar anti-flu compositions, however they are unable to decrease certainly the time of pathology and only in somehow relieve the symptoms of viral processes, but not significantly shorten the duration of the process. Another drawback of existing anti-flu drugs is the coexistence of undesired side effects, with a high impact in many cases, avoiding or limiting their use in people with chronic concomitant diseases.

DESCRIPTION OF THE INVENTION

The invention proposes a new natural pharmaceutical composition, without any side and adverse effects, which reduces significantly the duration of flu infection and additionally has properties as immunostimulant and antioxidant.

The invention relates to a botanical composition wherein the found synergism by mixing of plant extracts of *Echinacea purpurea* and *Myrciaria dubia*, which contain metabolites as echinacoside, cichoric acid, caftaric acid, rutin, quercetin, apigenin, caffeic acid, glycine betaine, equinadiol, gallic acid and ascorbic acid results in an unexpected finding, causing the interruption of flu infection, as well as an enhancement of the immune response to the infectious processes in a mammal wherein the mammal is a human.

The major components of this composition are dry extracts from *Echinacea purpurea* and *Myrciaria dubia*, whose ingredients primary and/or secondary metabolites, act with a synergism non previously reported, and in a weight ratio from 4% to 40% of *Myrciaria dubia* and from 30% and 80% of *Echinacea purpurea*, achieving to reduce the evolution period of flu to 3-4 days versus 10-15 days of this pathology in common conditions, with the traditional use of products that do not work on the flu and only are analgesic, anti-inflammatory or anti-pyretic products.

A component of the invention is the extract of *Myrciaria dubia*, wherein the ellagic acid acts synergistically with cichoric acid, echinacoside acid and cyanidin-3-glucoside achieving to reduce the lifetime of influenza by 70%.

The ellagic acid inhibits the aldolase reductase and its derivative the methyl ellagic has stronger inhibition than the quercetin (Ueda H. Et. al Kobe Pharmaceutical University, November 2004). Isolated compounds from *Myrciaria dubia*, prevent the formation of cataracts and the antioxidant property of this plant supports the criteria of this invention.

The composition according to the invention contains the fruits extracts of *Myrciaria dubia* collected in pre-maturing state when its peel has a green tone at 70% and a faint reddish colouring on its surface; under these conditions it undergoes dehydration wherein the temperature should not exceed 65 degrees Celsius for a period of 72 hours, a condition with which is achieved to maintain the suitable metabolite concentrations which later will act in the physiology of a mammal wherein the mammal is human. Subsequently, the product is powdering obtaining a dry extract which contain vitamin C and in addition has the metabolites object of this composition.

The dry extract of *Echinacea* sp., has a content of flavonoids such as quercetin calculated in around 0.48%, and alkylamides in around 4.1 mg/g.

The effect found in this invention is shown when the mixture of extracts is carried out with plants such as *Echinacea angustifolia, Echinacea pallida, Thuaja occidentalis, Echinacea purpurea, Chenopodium quinoa*, preferably *Myrciaria dubia* and *Echinacea purpurea* in a ratio of 1:4 to 9 by weight.

The invention is referred to the field of natural compositions, particularly herbal compositions to alleviate the effects, treat and reduce the duration of influenza as well as the infections caused by microorganisms which affect a human being.

An effective treatment for a variety of diseases caused by viruses and bacteria has been highly desired in both antiviral and antimicrobial actions, and in terms for relief of symptoms. Some Chinese or Ayurvedic herbal medicines have been found with some effectiveness in this field.

According to the invention an effective composition is provided due to the synergism of certain metabolites of the active ingredients in the extract mixture of the plants.

*Echinacea purpurea*, with active ingredients cichoric acid, alkylamides, echinacoside, chlorogenic acid, isochlorogenic acid, cinarine, caftaric acid, in a weight ratio of 10:1 of the extract of this plant to *Myrciaria dubia* whose active ingredients ellagic acid, alpha-pinene, d-limonene, bioflavonoids, beta-carotene and ascorbic acid, achieve a reduction of viral infection symptoms, and a shortening of the evolutive history of the viral or bacterial pathology.

In a preferred embodiment the active ingredients are cichoric acid in a proportion of 0.3 to 0.8% and ellagic acid in a proportion of 0.004% to 0.04%.

In addition to the active ingredients, the composition of the invention may have any number of inert ingredients which depend upon the particular form in which the complex can be administered to humans. Among these inert ingredients, it could be quoted lactose monohydrate, corn starch, croscarmellose sodium, sucralose, fructose, flavors, magnesium stearate, bioflavonoids, amino acids and silicon dioxide.

In a preferred embodiment the inert ingredients are in the following proportions:
lactose monohydrate between 19.23% to 49.23%
corn starch between 0.05% to 0.80%
croscarmellose sodium between 0.10% to 0.80%
sucralose between 0.92% to 4.92%
magnesium stearate from 0.15% to 0.35%
silicon dioxide between 0.095% to 0.25%

The natural composition object of the invention produces an unexpected effect on a variety of microorganisms.

Then, one of the object of the invention is the preparation of a compound that does not contain conventional components in the treatment of influenza and flu, such as ephedrine, caffeine, or the like and related components; which are undesirable components for the great majority of human beings who have developed resistance processes or sensitivity to these molecules.

An additional object is to provide a composition, in which among others, including actions for alleviating the influenza and flu symptoms and improve the ability of resilience of human organism against viral and bacterial infections.

Additionally, the provided composition protects healthy humans that are in contact with infected humans by influenza virus.

For the better exposure of the invention it shows examples of embodiments to carry out the invention without being a limitation of the scope of the same.

Example 1

This example illustrates the composition of the invention without being any limitation of the components or for the different administration forms.

| Extract *Myrciaria dubia* | 4.00% to 40.00% |
| --- | --- |
| Extract *Echinacea purpurea* | 30.00% to 75.00% |
| Excipient 1 | 0.030% to 0.080% |
| Lactose monohydrate | 19.23% to 49.23% |
| Cornstarch | 0.05% to 0.80% |
| Croscarmellose sodium | 0.10% to 0.80% |
| Sucralose powder | 0.92% to 4.92% |
| Flavor | 0.05% to 0.70% |
| Magnesium stearate | 0.15% to 0.35% |
| Colloidal Silicon Dioxide | 0.095% to 0.25% |

Example 2

Synergism Studies 21 volunteers, 12 men and 9 women between 20 and 45 years old, with initial influenza-like symptoms were observed, without any concomitant pathology. Patients were divided in 3 groups which received different treatment in the following manner.

Group I: 12 patients (5 women and 7 men) were subjected to a treatment with the composition according to the invention. The composition was administered every 8 hours.

Group II: 4 patients (2 women and 2 men) were treated with a composition containing as active ingredient only *Echinacea purpurea*. The compound was administered every 8 hours.

Group III: 5 patients (2 women and 3 men) were administered every 8 hours a dose of a composition containing *Myrciaria dubia* extract as active ingredient.

Results

Group I patients treated with a composition containing, as active ingredient, such extracts of *Echinacea purpurea* and *Myrciaria dubia* according to the invention, in a period of about 3 days, in 12 patients was observed an interruption of the classic symptomatology.

In Patients of Group II who were treated with a composition of *Echinacea purpurea*, was observed that the flu infection lasted about 7 days.

For Group III patients treated with a composition of *Myrciaria dubia*, the flu infection lasted about 5 days.

Alternatively, the composition according to the invention was administrated to people who were in family relationship with affected persons. The total number of people to whom the product was administrated have not been infected by the viral pathology.

Example 3

Comparative Studies with Other Drugs

Were further analyzed 10 volunteer patients, with an average age of 30 years old, without any concomitant pathology. 4 patients did not receive any medical treatment and 6 patients were treated with conventional anti-viral or anti-flu drugs.

Results

For 4 patients (3 men and 1 woman) who did not receive any medical treatment, the period of duration of the flu infection was approximately 15 days.

For patients who were medicated with conventional anti-flu drugs, the duration of the flu infection was between 10 and 12 days and for those who were treated with antiviral, the flu lasted for a period of about 6 days.

Example 4

According to this study, the reference time of lasting for a classic flu infection and the effect of the different components alone and in combination thereof and conventional anti-flu drugs, behaves as follows.

| PRODUCT | REFERENCE TIME OF LASTING FOR A FLU INFECTION |
| --- | --- |
| Echinacea purpurea | 7 days +/− 2 days |
| Myrciaria dubia | 5 days +/− 1 day |
| Combination of: Echinacea purpurea and Myrciaria dubia | 3 days +/− 1 day |
| Conventional Products: mixture of analgesics, antipyretics | 12 days +/− 2 days |
| Antiviral-based products | 6 days +/− 2 days |

From previous developed studies is also evidenced that patients treated with the composition according to the invention did not showed secondary effects as result of the drug administration. Thus, the composition provided in the invention does not have any side or adverse effects, also not finding any toxic effects on the body.

For a better understanding and clarity of the effectiveness of the proposed composition and the obtained results, we would like to illustrate these results through graphics.

Results of studies conducted in connection with the superior effect in the treatment of flu infections by the combination of Echinacea purpurea and Myciaria dubia are shown, according to the invention, in comparison with the effect obtained for each compound separately, whereof the potentiating effect of the anti-flu activity surprisingly obtained by the combination of the compounds is demonstrated.

Figure 1:
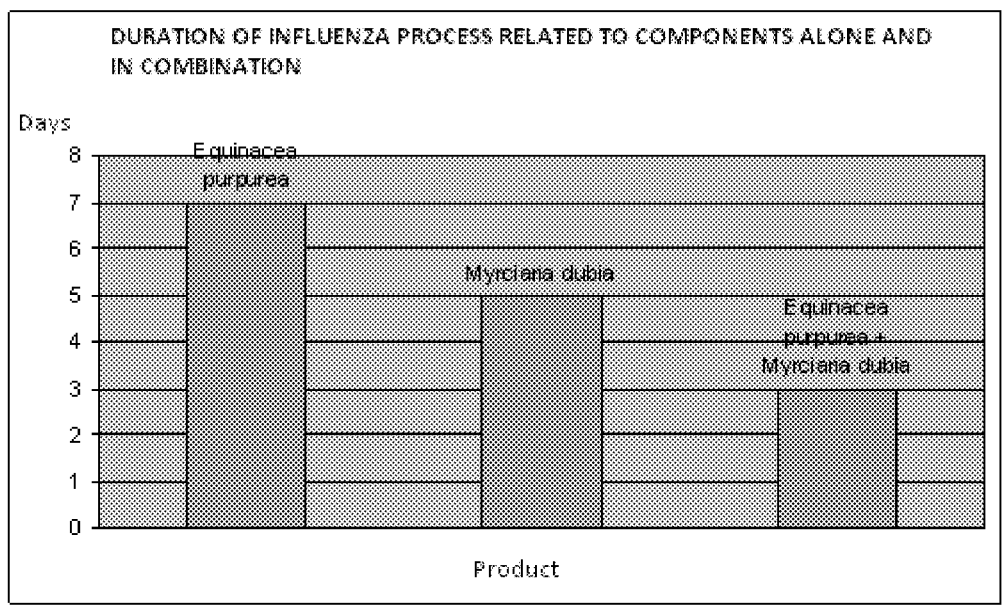
FIG. 1: Graphic A showing the synergistic effect of the proposed combination of the invention.
Figure 2:
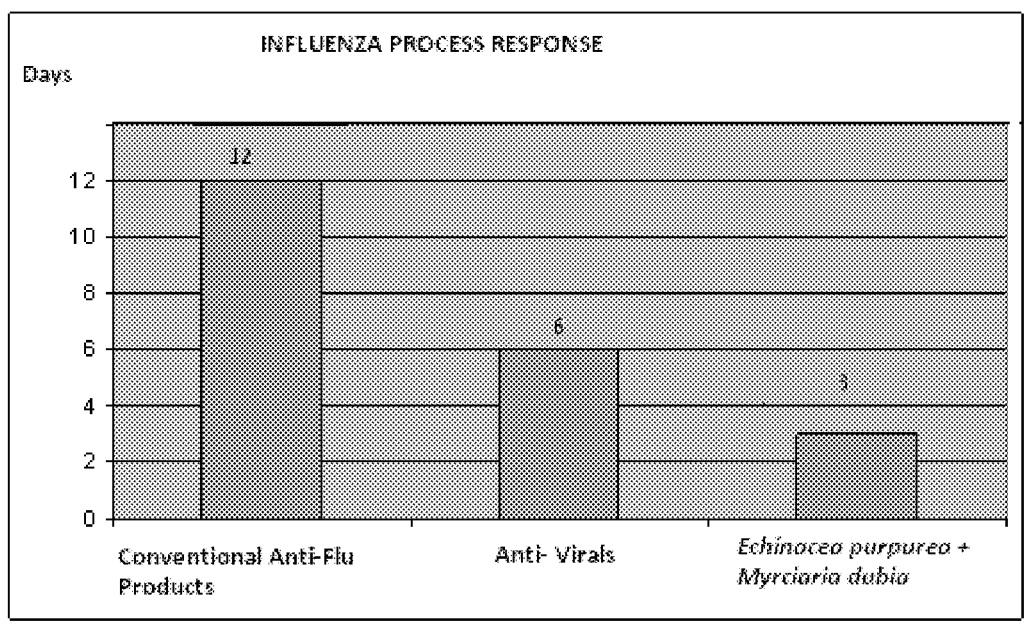

FIG. 2 shows the effectiveness of the proposed combination in the invention in the treatment of flu infections compared with the use of conventional drugs, according to the above developed studies.

The invention claimed is:

1. A synergistic composition for the treatment of influenza comprising effective amounts of:
   a) an extract of Echinacea purpurea containing cichoric acid in an amount of 0.3 to 0.8% therein;
   b) an extract of Myrciaria dubia containing ellagic acid in an amount of 0.004 to 0.04% therein; and
   c) one or more inert ingredients,
   wherein the extracts of Echinacea purpurea and Myrciaria dubia are in a ratio of 1:4-9 within the composition.

2. The synergistic composition according to claim 1, wherein the amount of the extract of Myrciaria dubia is between 4 to 40% of total weight of the composition.

3. The synergistic composition according to claim 1, wherein the amount of extract of Echinacea purpurea is between 30 to 75% of total weight of the composition.

4. The synergistic composition according to claim 1, wherein each of the extracts of Echinacea purpurea and Myrciaria dubia further contain active components selected from the group consisting of alkylamides, echinacoside, verbascocide, chlorogenic acid, isochlorogenic acid, cynarine, caftaric acid, alpha-pinene, limonene, citric acid and beta carotene.

5. The synergistic composition according to claim 1, wherein the one or more inert ingredients are selected from the group consisting of lactose monohydrate, corn starch, croscarmellose sodium, sucralose, fructose, flavors, magnesium stearate, bioflavonoids, amino acids, and silicon dioxide.

6. The synergistic composition according to claim 5, wherein the one or more inert ingredients comprises lactose monohydrate in an amount of between 19.23 to 49.23% of the total weight of composition.

7. The synergistic composition according to claim 5, wherein the one or more inert in ingredients comprises corn starch in an amount of between 0.05 to 25 0.80% of the total weight of the composition.

8. The synergistic composition according to claim 5, wherein the one or more inert ingredients comprises croscarmellose sodium in an amount of between 0.10 to 0.80% of the total weight of the composition.

9. The synergistic composition according to claim 5, wherein the one or more inert ingredients comprises sucralose in an amount of between 0.92 to 4.92% of the total weight of the composition.

10. The synergistic composition according to claim 5, wherein the one or more inert ingredients comprises magnesium stearate in an amount of between 0.15 to 0.35% of the total weight of the composition.

11. The synergistic composition according to claim 5, wherein the one or more inert ingredients comprises silicon dioxide in a concentration between 0.095 to 0.25% of total weight of the composition.

12. A method for treating a patient having influenza comprising administering to said patient an effective amount of the synergistic composition according to claim 1.

* * * * *